(12) United States Patent
Gatzemeyer et al.

(10) Patent No.: US 8,499,397 B2
(45) Date of Patent: Aug. 6, 2013

(54) ORAL CARE IMPLEMENT WITH CUSTOMIZABLE ELEMENT

(75) Inventors: John Gatzemeyer, Hillsborough, NJ (US); Eduardo Jimenez, Manalapan, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/416,694

(22) Filed: Mar. 9, 2012

(65) Prior Publication Data

US 2012/0159723 A1  Jun. 28, 2012

Related U.S. Application Data

(62) Division of application No. 12/159,313, filed as application No. PCT/US2008/065700 on Jun. 4, 2008, now Pat. No. 8,161,591.

(51) Int. Cl.
*A46B 5/00* (2006.01)
*A46B 15/00* (2006.01)
*A61C 17/22* (2006.01)

(52) U.S. Cl.
USPC ............ 15/22.1; 15/105; 15/143.1; 15/167.1; 15/246; 40/314; 40/661.12; 40/442; 362/119; 362/120; 446/71

(58) Field of Classification Search
USPC ....... 15/22.1, 105, 143.1, 167.1, 246; 40/314, 40/661.12, 442, 913; 174/66, 67; 362/119, 362/120; 446/71, 73, 76, 321; 434/263
See application file for complete search history.

(56) References Cited

U.S. PATENT DOCUMENTS

| | | | |
|---|---|---|---|
| 876,317 A | 1/1908 | Booth | |
| 1,211,468 A | 1/1917 | McLean | |
| 1,380,633 A | 6/1921 | Brown | |
| 2,016,644 A | 10/1935 | Luball | |
| 2,187,192 A | 1/1940 | Albrecht | |
| 4,571,199 A * | 2/1986 | Murakami | 446/73 |
| 4,589,159 A | 5/1986 | Streibel | |
| 5,010,665 A * | 4/1991 | Clinkscales | 40/1.5 |
| 5,259,086 A | 11/1993 | Fong | |
| 5,337,435 A * | 8/1994 | Krasner et al. | 15/23 |
| 5,590,436 A | 1/1997 | Wright et al. | |
| D448,175 S | 9/2001 | Shurney | |

(Continued)

FOREIGN PATENT DOCUMENTS

| | | |
|---|---|---|
| DE | 2826008 | 12/1979 |
| EP | 0683995 | 11/1995 |
| WO | WO 2006/003598 | 1/2006 |
| WO | WO 2007/122491 | 11/2007 |

OTHER PUBLICATIONS

International Search Report for International Application No. PCT/US2008/065700 mailed Nov. 27, 2009.

*Primary Examiner* — Mark Spisich
(74) *Attorney, Agent, or Firm* — Ryan M. Flandro

(57) ABSTRACT

An oral care implement with an oral care region having cleaning elements for engaging oral tissue and a body for gripping the implement including a handle with a front and a removable faceplate is described. The removable faceplate may be transparent or translucent and may also include design features. The faceplate may provide protection to a user inscription surface on one of the surfaces of the handle which is may be configured to receive user indicia that may later be removed and further indicia provided.

9 Claims, 6 Drawing Sheets

U.S. PATENT DOCUMENTS

| | | |
|---|---|---|
| 6,699,038 B2 | 3/2004 | Stewart |
| 6,779,216 B2 | 8/2004 | Davies et al. |
| 2003/0019063 A1 | 1/2003 | Abraham |
| 2004/0139569 A1 | 7/2004 | Chen |
| 2004/0236628 A1 | 11/2004 | Kemp |
| 2005/0044646 A1 | 3/2005 | Peretz et al. |
| 2005/0125920 A1 | 6/2005 | Hui et al. |
| 2005/0198754 A1 | 9/2005 | Dai |
| 2006/0225231 A1 | 10/2006 | Jimenez et al. |
| 2006/0230652 A1 | 10/2006 | Little |
| 2006/0288504 A1 | 12/2006 | Banning |
| 2007/0050931 A1 | 3/2007 | Jimenez et al. |
| 2007/0094822 A1 | 5/2007 | Gatzerneyer |

* cited by examiner

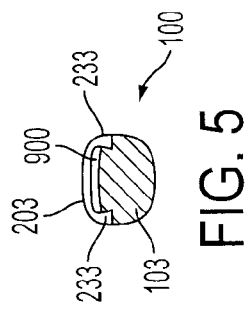
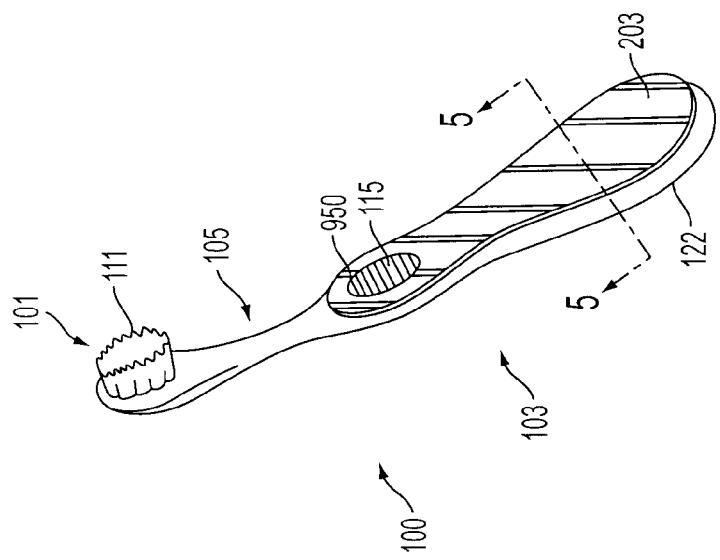
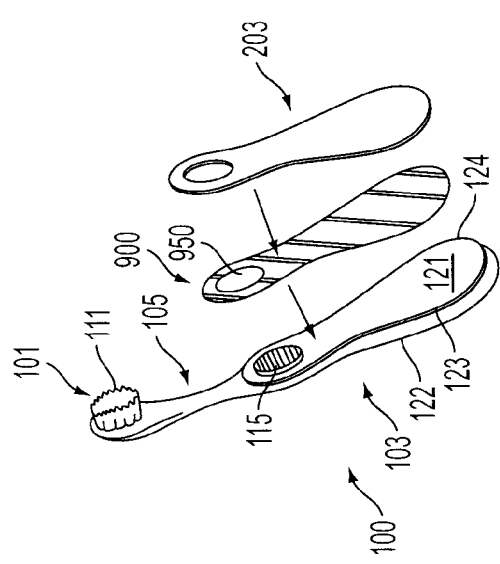

ORAL CARE IMPLEMENT WITH CUSTOMIZABLE ELEMENT

CROSS-REFERENCE TO RELATED APPLICATIONS

The present application is a divisional of U.S. patent application Ser. No. 12/159313, filed on Jun. 26, 2008, now U.S. Pat. No. 8,161,591, which is a national stage entry under 35 U.S.C. §371 of International Patent Application No. PCT/US2008/065700, filed Jun. 4, 2008, the entireties of which are incorporated herein by reference.

BACKGROUND

The present invention pertains to an oral care implement, in particular, to a toothbrush with a customizable element. Individuals exhibit many forms of poor oral health including tooth decay, periodontal diseases and bad breath (halitosis). Tooth decay and periodontal disease are typically caused by harmful bacteria within the mouth. When the harmful bacteria mixes with proteins present in saliva, a film of plaque is formed on the teeth and soft tissue. If the plaque is not removed, it can attack the teeth and create cavities. Additionally, the plaque will attack the soft tissue within the mouth and cause gum disease, the leading cause of tooth loss in adults. Many individuals, especially young children, do not regularly brush their teeth or perform interdental cleaning of their teeth. Such habits may be attributed to the individual regarding tooth brushing as a mundane duty with few pleasurable aspects.

BRIEF SUMMARY

The present invention pertains to an oral care implement with a customizable element.

In one aspect, an oral care implement, with an oral care region having cleaning elements for engaging oral tissue and a body for gripping the implement including a handle with a front and a removable faceplate is described. The removable faceplate may be transparent or translucent and may also include design features. The faceplate may provide protection to a user inscription surface on one of the surfaces of the handle which may be configured to receive user indicia that may later be removed and further indicia provide.

In another aspect, a motorized electric oral care implement, with an oral care region having cleaning elements for engaging oral tissue, a body for gripping the implement including a handle having a removable faceplate, and an electric power source, such that the faceplate is electrically coupled to the electrical power source when the faceplate is in an attached state is described. The power source powers visual and/or audio features of the faceplate providing entertainment and interest to the user.

Other features and advantages of the invention will become apparent from the following description taken in conjunction with the following drawings.

BRIEF DESCRIPTION OF THE DRAWINGS

FIGS. 3 and 4 are illustrative perspective views of the toothbrush having a handle for displaying a customized printing in a disassembled and assembled state, respectively;

FIG. 5 is an illustrative bottom view of the toothbrush of FIG. 4, taken along line 5-5;

DETAILED DESCRIPTION OF PREFERRED EMBODIMENTS

In the following description, certain embodiments are discussed in terms of a toothbrush (e.g. a form of an oral care implement), but could be in the form of other personal care implements. For example, a toothbrush can be used for personal hygiene, such as oral care purposes. Further, it is understood that other embodiments may be utilized and structural and functional modifications may be made without departing from the scope of the present invention.

Figure 1:
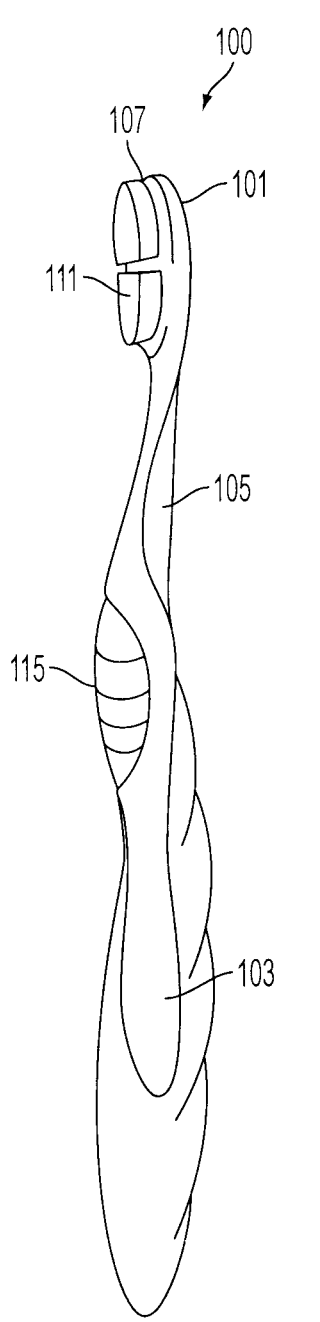
FIGS. 1 and 2 are perspective front and rear views of one embodiment of an oral care implement, such as a toothbrush.
Figure 2:
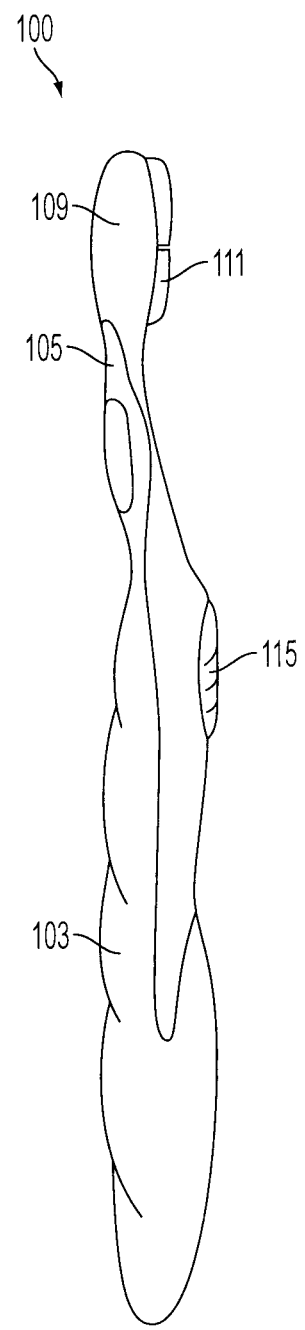

FIGS. 1-2 illustrate an oral care implement, such as a toothbrush, generally designated with the reference numeral 100. The toothbrush 100 generally includes a head 101 and a handle 103.

The handle 103 is generally an elongated member dimensioned so that a user can readily grip and manipulate the toothbrush 100. The handle 103 may be formed of many different shapes, lengths and with a variety of constructions. In one construction, the handle 103 has a neck portion 105 positioned adjacent the head 101. The neck portion 105 may be a narrowed region on the handle 103 between head 101 and the part of the handle normally gripped by the user. Nevertheless, the neck portion 105 could be the region between the head 101 and the part of the handle normally gripped by the user. In another construction, the handle 103 is integrally formed with the head 101. Other attachment configurations also are possible.

The head 101 may include an oral care region comprising one or more tooth cleaning elements 111. As used herein, the term "tooth cleaning elements" or "cleaning elements" includes any type of structure that is commonly used or is suitable for use in providing oral health benefits (e.g., tooth cleaning, tooth polishing, tooth whitening, massaging, stimulating, etc.) by making contact with portions of the teeth and gums. Such tooth cleaning elements include but are not limited to tufts of bristles that can be formed to have a number of different shapes and sizes, and elastomeric cleaning members that can be formed to have a number of different shapes and sizes, or a combination of both tufts of bristles and elastomeric cleaning members.

In one construction, the one or more tooth cleaning elements 111 are formed from a plurality of bristles. Referring to FIGS. 1 and 2, the tooth cleaning elements 111 are bristle regions having different shapes, however, it is understood that a number of different configurations of oral care implements may be utilized, The one or more tooth cleaning elements 111 may be attached to the head 101 by known methods, such as being fit within recesses formed in the head 101 along a front portion 107, opposite a back portion 109 of the toothbrush 100 (FIG. 1). The head 101 also may be configured to be detached from the neck 105 or handle 103 and replaced with a new head 101, if desired.

FIGS. 3-5 illustrate an alternative construction of toothbrush 100. In this construction, the toothbrush 100 is configured to facilitate user customizability by providing a visual design surface. The visual design surface may include any type of printing including graphics, design, articles, photographs, or other creations in a tangible medium, such as a paper type format, for example, shown and described herein as a customized printing 900. As illustratively shown by FIGS. 3-5, a handle 103 having a generally rectangular cross-section shape in this configuration may generally include a plurality of sides illustratively referred to as the front 121, the rear 122, the left side 123 and the right side 124. In order to facilitate extensive customizability in the appearance of the oral care instrument and in particular the handle 103 of the toothbrush 100, one or more sides of the handle 103 may be configured to house the visual design surface. Thus, any of the aforementioned types of printing can be provided on handle 103, and handle 103 further may be formed to hold, protect, and display the customized printing 900 provided by the user.

In order to house the customized printing 900, a faceplate 203 and at least one surface of the handle 103, for example, front 121, can be used to abut the customized printing on two opposing sides so as to hold, protect and/or display the customized printing. The visual design surface, which is customized printing 900 in the illustrated embodiment, is visible from an exterior of faceplate 203. Here, the front 121 of the handle 103 and faceplate 203 may be snapped together utilizing a fastening mechanism to hold these two complimentary components together. In certain embodiments, complimentary sizing causing frictional engagement of the exterior border of the faceplate 203 with a complimentary receiving footprint of the front 121 of the handle 103 can be used to cause a snap attachment to occur, as is well known.

It is noted that the faceplate 203 may be configured with internal protrusions or cut-outs. One such example is cut-out 950, shown in FIGS. 3 and 4. Cut-out 950 is formed to allow a control button 115 for a powered toothbrush to be manipulated by a user even if the faceplate 203 is attached, since the control button passes through the cut-out 950. Cutout 950 is an aperture configured to complimentary surround the control button 115 so as to not destroy the functionality of the toothbrush 100. Because the cut-out 950 may be sized to snugly fit around the control button 115, and may assist or completely perform the function of holding the faceplate 203 to the front 121 of the handle 103, it may also be considered in certain configurations as a fastening mechanism for holding the faceplate 203 to the front 121 of the handle 103 in order to display a customized printing 900, which is shown here with a complimentary cut-out 950 to allow for the control button 115 to remain accessible. Numerous other fastening mechanisms may be used, including any type of male and female mated components, snap, button, or screw attachment mechanisms as is appreciated in the art.

FIG. 5 is an illustrative bottom view of the toothbrush and illustrates one embodiment of the engagement of the faceplate 203 with the front 121 of the handle 103. Faceplate 203 here includes a pair of arms 233 that are complimentary shaped to frictionally engage the front 121 of the handle 103. Here, the arms 233 are shaped and the rigidity of the material, e.g. a plastic of any type well known in the art or other like materials used, provide for a snap fit onto the handle 103. The arms 233 hold the faceplate 203 on to the handle 103 and to front 121 thereby ensuring that the customized printing 900 is firmly secured to the toothbrush 100, and more particularly to handle 103. Further, depending on the specific configuration, the arms 233 or other fastening mechanisms may be formed to prevent particles from the environment, including moisture and water, from contacting the printing and potentially damaging the printing. For example, the customized printing may be sealed in a generally waterproof compartment when the faceplate 203 is attached to or engaged with handle 103.

For ease of explanation and understanding, the handle 103 and complimentary faceplate 203 used to house customized printing 900, as they are illustratively shown in FIG. 3, may be considered as being in a disengaged or disassembled or storage position. In contrast, FIGS. 4 and 5 are perspective and section views, respectively, of the handle 103, customized printing 900, and complimentary faceplate 203 in an engaged, assembled or in-use position.

To facilitate the display of the customized printing 900, the printing must be placed in a shape complimentary to the compartment in which it will be housed in handle 203. A customized printing may be purchased or otherwise acquired already in a shape suited for display in the handle of the toothbrush. Alternatively, any printing may be formed into an appropriate shape and sizing to be displayed in the described fashion. For example, faceplate 203 may be used as a template for tracing an outermost boundary of any printing. By cutting and/or forming the printing to the template shape and size, the user is able to configure practically any printing in a paper-like medium for placement in the handle 103 of the toothbrush 100. This extreme workability permits the described oral care assembly to possess virtually unlimited customizability for users to create oral care assemblies having desirable visual appearances, regardless of a user's particular style, taste, imagination or interest preferences.

Further, to facilitate viewing of the customized printing of a user, the faceplate in at least one configuration is transparent, such that the customized printing is visible from an exterior of the faceplate. In other embodiments, the faceplate may be translucent. As such the faceplate may be composed of any of the known generally transparent materials in the art including various plastics. Among the materials that may be utilized include Acrylic (polymethlamethacrylate), Butyrate (cellulose acetate butyrate), Lexan (polycarbonate), and PETG (glycol modified polyethylene terphthalate). However, numerous transparent and/or translucent materials may be utilized as is well know in the art. These transparent/translucent materials, including plastics, may be formed into shapes that are complimentary to the general shape of the handle 103, and more specifically the shape of the front 121 of the handle 103, to enable a complimentary fit as described herein. Further, the faceplate 203 may be composed of a transparent/translucent material that includes a design incorporated into the material as is known in the art. For example a colored pattern may be placed within the transparent material such that the pattern within the faceplate is visible to the user, while features, structures and indicia on an opposing side of the faceplate from the user are still recognizable, viewable and readable. Further, consistent with various desired themes as described herein the design incorporated herein in may be indicia of sports teams, celebrities, television, movie or radio programming and various other displays that would be of interest to a user.

Figure 6:
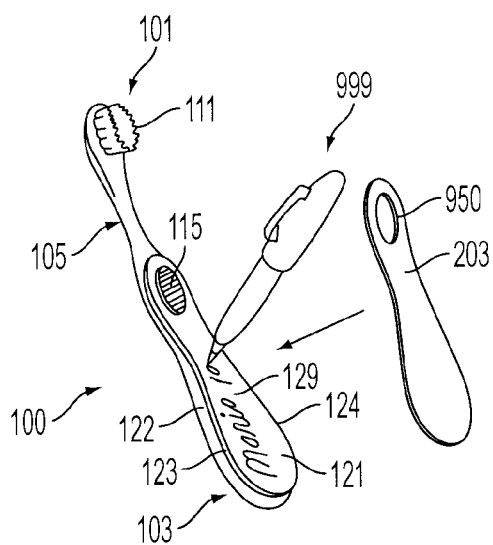
FIGS. 6 and 7 are illustrative perspective views of the toothbrush in another configuration for displaying customized printing in a disassembled and assembled state, respectively.
Figure 7:
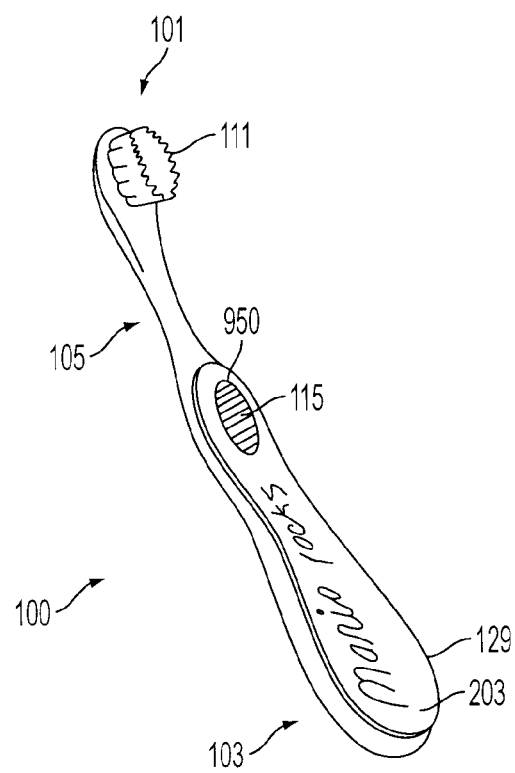

FIGS. 6 and 7 are illustrative perspective views of a toothbrush having a visual design surface in another configuration shown in disassembled and assembled states, respectively. In this configuration, user customizability is facilitated as the toothbrush 100 has a handle 103 with a visual design surface in the form of a user inscription surface 129 that permits a user to write, draw, color, sketch, paint or otherwise place indicia on toothbrush 100. Here, handle 103 houses the user inscription surface 129.

As shown in FIGS. 6 and 7, the user inscription surface 129 may be housed on the front 121 of the handle 103. As such, the user inscription surface 129 may be a portion of the front 121 of the handle 103 or may be the entire front 121 of the handle 103. Alternatively, although not depicted, the user inscription surface 129 may form the entirety of the handle 103 such that a user may write, draw, color, sketch, paint or otherwise place indicia on any portion of the handle 103 or even the entirety of the toothbrush, if the entirety of the toothbrush but for the cleaning elements 111 were formed as the user inscription surface 129. In FIGS. 6 and 7, the user inscription surface 129 is thrilled to form a substantial entirety of front 121. FIG. 6 illustrates the handle 103 in a disassembled state. In this disassembled state a user may write, draw, color, sketch, paint or otherwise place indicia on the user inscription surface 129 with any tool or implement, as long as a writing fluid can be received by the material that forms the user inscription surface 129.

Accordingly, the user inscription surface 129 may be made of any of a number of materials that are known in the art to receive writing, drawing, coloring, sketching, painting or otherwise placing indicia on a surface. For example, dry erase board materials may be used such that a user may use dry erase markers. Further, in at least one configuration the user inscription surface may be made of one of a melamine resin, polyester coated steel or enamel steel similar to the materials used in dry erase or whiteboards. Any writing surface and writing implement that allows for user customization, editing revision and/or erasure may be used with respect to the user inscription surface. User indicia implement 999 is shown in FIG. 6 to demonstrate one illustrative example of a user customizing the handle by writing on user inscription surface 129 of the handle 103. Of course, any other form of user customization may be performed consistent with what is shown here and what is known in the art.

Because dry erase and other materials often use water as the agent to cause or assist in erasing, and toothbrushes typically get wet when used, a toothbrush 100 having a handle 103 with a user inscription surface that is completely exposed when it is used may not be preferred by a user, as the customized indicia that the user has added to the handle 103 is likely to be smeared or erased by either the water that accumulates on the handle during use, or alternatively by smearing when a user grips the handle 103. Accordingly, the removable transparent cover 203 may be utilized and configured to protect the user inscription surface 129 when the handle 103 is in an assembled state, as is illustrated in FIG. 7. In the assembled state, the customized surface is viewable by the user, while the indicia itself on the user inscription surface 129 is substantially or completely protected from the user's grip, from water and/or from other environmental factors depending on the particular configuration. As described and as is known in the art, the fastening mechanism and the dimension of the handle 103 and faceplate 203 may be made such that water and other environmental elements may be prevented from contacting the user inscription surface. Thus, a customizable and modifiable handle 103 is provided that is protected by the faceplate 203 from damage or erasure. Further, the customizable and modifiable handle 103 may be edited or completely changed by removing the faceplate 203 and erasing the previous indicia, and replacing it with new indicia (e.g placed in disassembled state and then edited). Then, when the toothbrush 100 is to be used, the faceplate 203 is reattached placing the handle 103 and toothbrush 100 in an assembled state.

Figure 8:
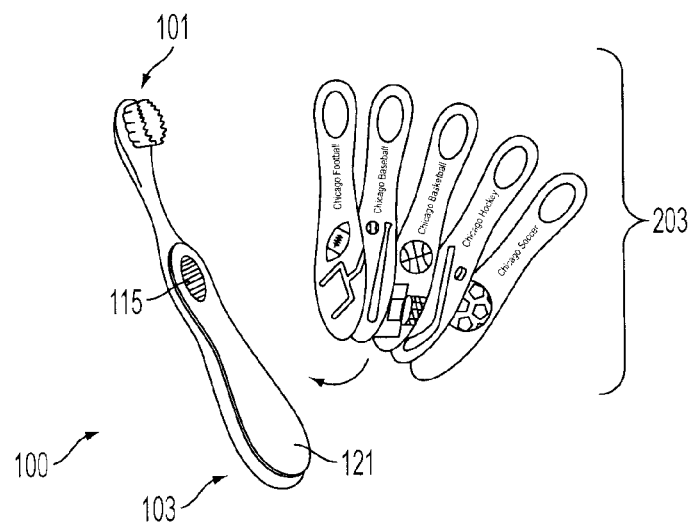
FIGS. 8 and 9 are illustrative perspective views of the toothbrush in another configuration for displaying customized printing in a disassembled and assembled state, respectively.
Figure 9:
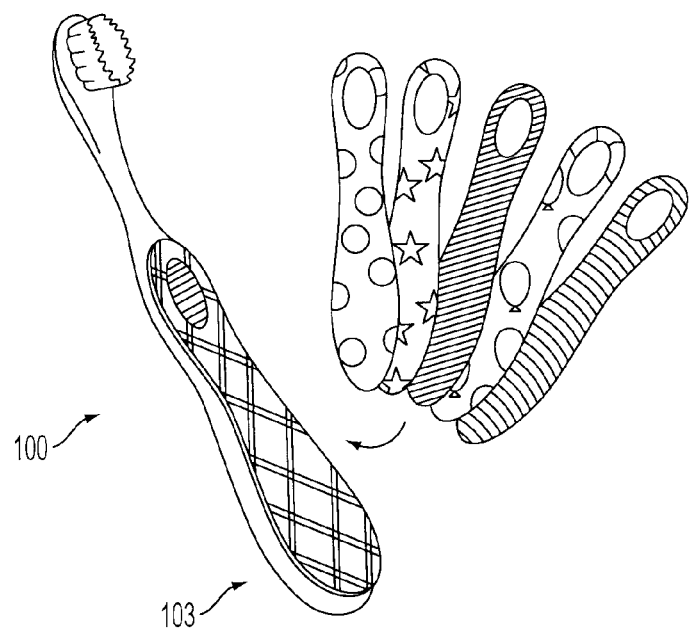

FIGS. 8 and 9 are illustrative perspective views of the toothbrush 100 in another configuration for displaying customized printing in a disassembled and assembled state respectively. Similar to the previous described configurations, the illustrated toothbrush 100 may include a faceplate 203 complimentarily configured to the handle 103 so as to fit together in an assembled position. Here, a wide variety of thematic faceplates 203 are contemplated such that users, for example, children or sports fans, may collect a series of faceplates and use them in alternating fashion. For example, a series of faceplates 203 might include all the characters from a cartoon such that each faceplate 203 includes a design specific to a certain character in the cartoon. As the user desires, the faceplates may be used in alternative fashion depending on the user's desires, preferences, and entertainment wishes. Another illustrative example consistent with these principles is a sports series of faceplates 203. Oftentimes sports fans support many of the sports teams from a given city. For example, a sports fan in Chicago may support the large sports team from Chicago. These teams may include the Chicago Cubs, Chicago Bears, Chicago Bulls, and the Chicago Blackhawks. The same would be the case for someone from Washington, D.C. They might desire Washington Redskins, Washington Wizards, Washington Nationals, and Washington Capitals faceplates such that, depending on what time of year it is, the faceplate on their toothbrush 100 would display support for a different one of those teams. Alternatively, individual faceplates may be made and/or traded similar in fashion to when baseball or other sports trading cards are purchased and traded. Accordingly, a series of faceplates may be packaged and sold with or without a toothbrush configured and dimension such that the faceplate(s) 203 fits in complimentary fashion on the toothbrush. While the principles have been demonstrated herein with respect to the above examples, any thematic principle may be used consistent with the principles described herein to provide entertainment or artistic and creative expression.

Figure 10C:
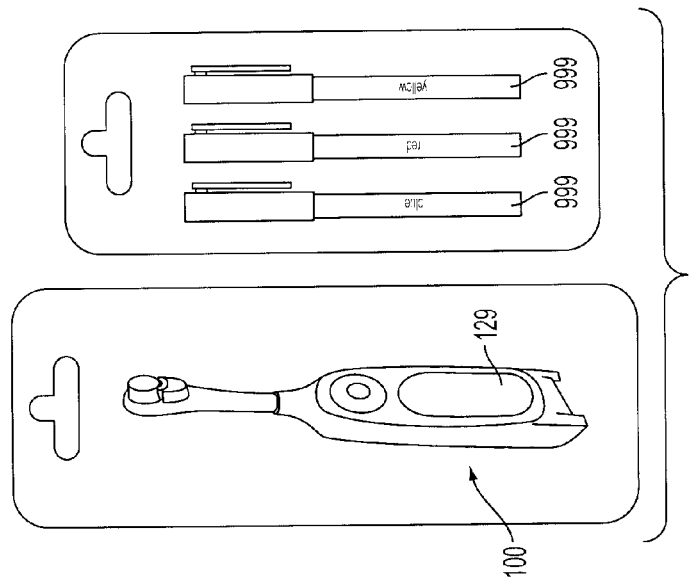
FIGS. 10A-C are illustrative configurations of a method of marketing a customizable toothbrush and/or its complimentary faceplate.
Figure 10B:
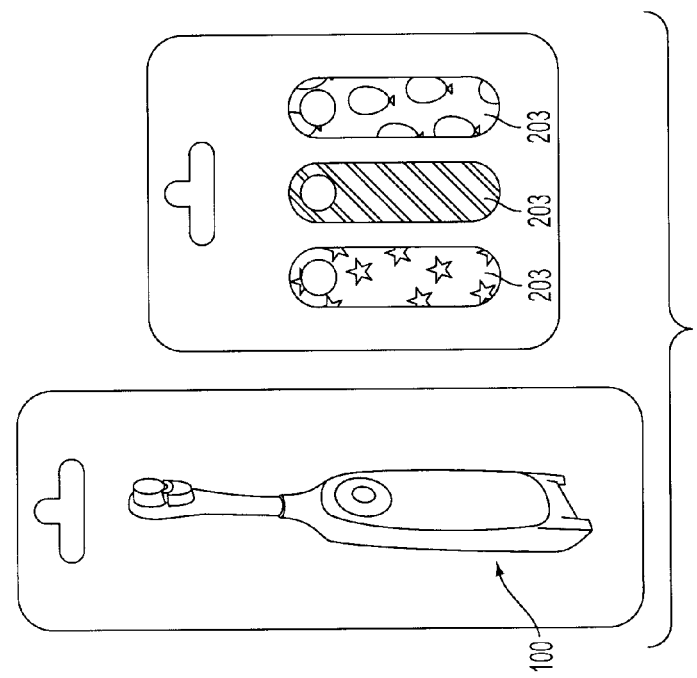
Figure 10A:
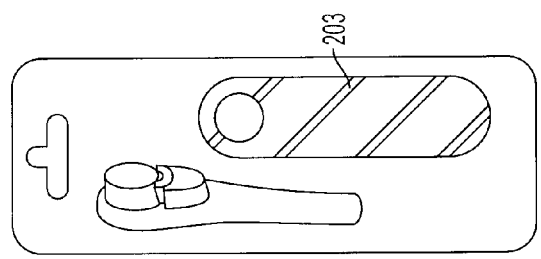

FIGS. 10A-C are illustrative configurations of a method of marketing a customizable toothbrush 100 and/or its complimentary faceplate 203. In FIG. 10A, an illustrative package containing a faceplate 203 and a replacement head for a motorized electrical toothbrush 100 is shown. Consistent with the principles described above, the faceplate 203 may be configured to have any of numerous graphic designs, colorings or thematic appearances for entertainment of the purchaser. FIG. 10B illustrates marketing and sales of a toothbrush 100 with a series of thematically related faceplates 203. Thus the purchaser selects the type of toothbrush and then can select from various pre-packaged sets of faceplates 203. One illustrative set is shown in which the theme is a location-based sports theme, e.g. Chicago sports teams. Thus, one particular type of toothbrush 100 may be manufactured, however, it is customizable to practically any user depending on the user's interest, location or style. Accordingly, a user-customized toothbrush is provide while still keeping manufacturing costs down, since a generic toothbrush is modified by user identification and selection of faceplates 203 that fit on complimentary fashion on the toothbrush 100. Also, FIG. 10C illustrates marketing of a toothbrush 100 with a handle 103 having a user inscription surface 129 in a single package, along with a plurality of varying indicia implements 999 that the user may use to write, draw, color, sketch, paint or otherwise place indicia on the user inscription surface 103. Additionally, as described above, the toothbrush 100 in at least one configuration is uniquely customizable to a user. With the toothbrush 100 and the customizable faceplate 203 in hand, a user can acquire or form any graphic, etc., that is in a paper-like medium, into a shape and size complimentary with the toothbrush 100 and faceplate 203. In some instances, this may be accomplished by purchasing a pre-formed customized printing 900 or may be accomplished by forming any printing into the requisite shape and size by using the faceplate 203 or other portions of the toothbrush 100 as a template. As described, there are numerous methods of marketing or selling the described customizable toothbrush 100 for user enjoyment and entertainment.

Figure 11:
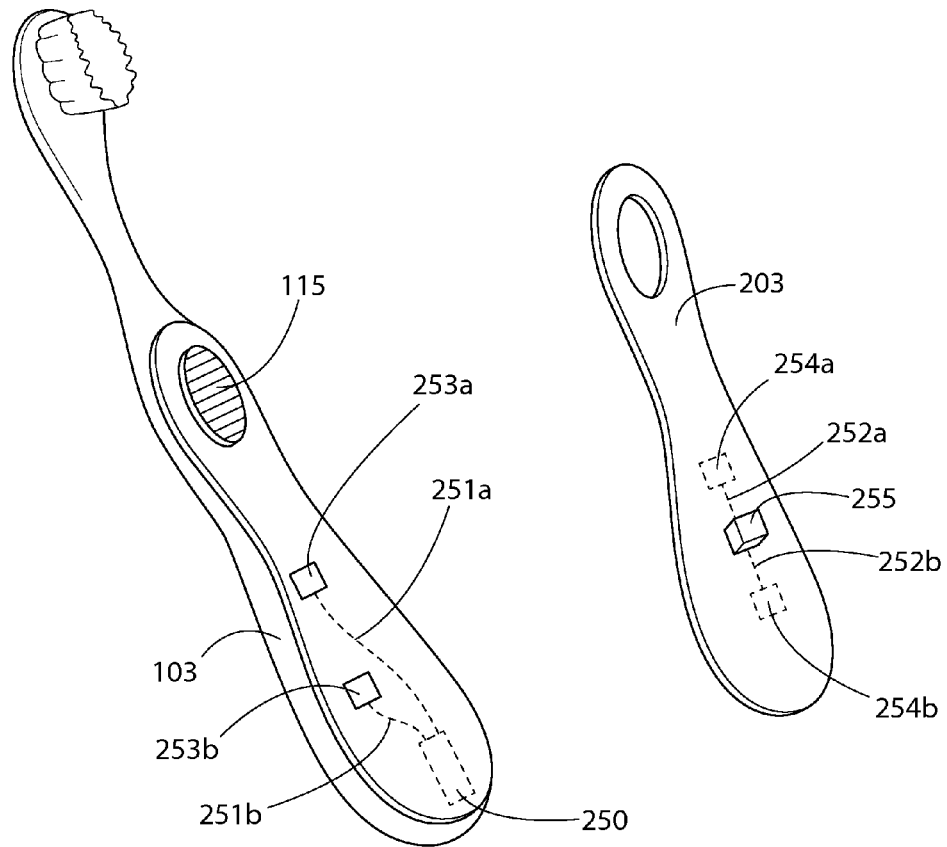
FIG. 11 is an illunstrative perspective view of the toothbrush and faceplate with electrical connectors.

While the described customization has been applicable to oral care implements of practically any variety or type, a motorized electrical oral care implement such as a motorized electrical toothbrush enables further customizability in compliment with an electrical power source 250. For example, referring to FIG. 11. the handle 103 as well as any of the various faceplates 203 may be complementary configured to house electrical connectors 253a,b and 254a,b and electrical leads 251a,b and 252a,b to allow for an electrical circuit to be formed and electrical power from the electrical power source 250 to be supplied to a powered feature 255 of the faceplate 203. As such, faceplates 203 may have illumination, sound picture or other entertainment features that are reliant on electrical power. Faceplates 203 may be configured so when they are in an assembled state they are powered, and when they are in a disassembled state they are not powered Further, the faceplates may be electrically wired such that when the control button 115 of the toothbrush is in an on position, the toothbrush is powered and the cleaning elements are moved, but also the faceplate is powered and energized. Accordingly, the faceplate 203 may display blinking lights, animation, music and virtually any other entertaining stimulus. Accordingly, users of the toothbrush may be encouraged to spend time on oral care since there is an entertainment incentive to extend use of the oral care instrument. Even further, sophisticated oral care instruments may even be formed in accordance with the above described principles wherein the faceplate 203 houses a portable audio player, such as an MP3 player or similar music player. Likewise, an LCD display screen may he housed in the faceplate such that video imagery or audio and video imagery is displayed on the oral care instrument. Since many electrical toothbrushes are plugged in from time to time in a wall outlet in a bathroom, such an oral care instrument could efficiently serve as a visual or audio entertainment source in a bathroom, much the way certain homes or hotels have radios or televisions in bathrooms to provide entertainment while people shower, apply make-up or otherwise prepare for their day.

As discussed, the inventive aspects are described in reference to any oral care instrument and may also be specifically practiced by a manual toothbrush or a powered toothbrush with moving tooth cleaning elements 111. While the various features of the toothbrush 100 work together to achieve the advantages previously described, it is recognized that individual features and sub-combinations of these features can be used to obtain some of the aforementioned advantages without the necessity to adopt all of these features.

While the invention has been described with respect to specific examples including presently preferred modes of carrying out the invention, those skilled in the art will appreciate that there are numerous variations and permutations of the above described systems and techniques. Thus, the spirit and scope of the invention should be construed broadly as set forth in the appended claims.

We claim:

1. A motorized electric oral care implement, comprising:
an oral care region having cleaning elements for engaging oral tissue;
a body for gripping the implement including a handle having a removable faceplate, the faceplate overlying at least a portion of a major surface of the handle when the faceplate is in an attached state;
an electric power source within the handle; and
wherein the faceplate and the handle are complementary configured with electrical connectors so that the faceplate is electrically coupled to the electrical power source when the faceplate is in the attached state and further wherein the faceplate includes a feature that is powered by the electrical power source when the faceplate is in the attached state.

2. The motorized electric oral care implement of claim 1, wherein the feature includes at least one of an illumination, graphic, and sound feature.

3. The motorized electric oral care implement of claim 2, wherein the feature is one of an LCD screen and a portable music player.

4. The motorized electric oral care implement of claim 1 wherein activation of the motorized electric oral care implement moves the cleaning elements and activates the feature.

5. The motorized electric oral care implement of claim 4, wherein deactivation of the motorized electric oral care implement deactivates the feature and the movement of the cleaning elements.

6. The motorized electric oral care implement of claim 1, wherein the electrical power source is a battery.

7. The motorized electric oral care implement of claim 1, wherein the faceplate is not powered when the faceplate is in a disassembled state such that the faceplate is separated from the major surface of the handle.

8. The motorized electric oral care implement of claim 1, wherein the major surface of the handle is a front surface of the handle.

9. The motorized electric oral care implement of claim 8 wherein the feature is an illumination feature and further comprising a control button on the front surface of the handle, and wherein when the control button is in an on position, the cleaning elements are moved and the illumination feature on the faceplate is activated.

* * * * *